United States Patent [19]

Schultz

[11] 4,034,755
[45] July 12, 1977

[54] SYRINGE

[75] Inventor: Harold R. Schultz, Sparks, Nev.

[73] Assignee: Hamilton Company, Reno, Nev.

[21] Appl. No.: 613,940

[22] Filed: Sept. 16, 1975

[51] Int. Cl.² .......................................... A61M 5/00
[52] U.S. Cl. ............................ 128/216; 128/218 C; 222/387
[58] Field of Search ....... 128/218 R, 218 C, 218 D, 128/218 N, 218 NJ, 215, 220, 221, 216; 222/386, 387

[56] References Cited

U.S. PATENT DOCUMENTS

| 1,240,033 | 9/1917 | Dickinson | 128/218 N |
| 2,554,451 | 5/1951 | Barry | 128/220 |
| 3,063,450 | 11/1962 | Myerson et al. | 128/218 D |
| 3,417,904 | 12/1968 | McLay | 128/218 C |
| 3,677,448 | 7/1972 | Harris, Sr. et al. | 222/387 |

Primary Examiner—John D. Yasko
Attorney, Agent, or Firm—Fitch, Even, Tabin & Luedeka

[57] ABSTRACT

A syringe is described in which the needle assembly thereof is manually adjustable axially with respect to the body of the syringe to line up one end of the needle assembly with a reference mark on the transparent hollow barrel. Means are provided for locking the position of the needle assembly with respect to the body.

8 Claims, 1 Drawing Figure

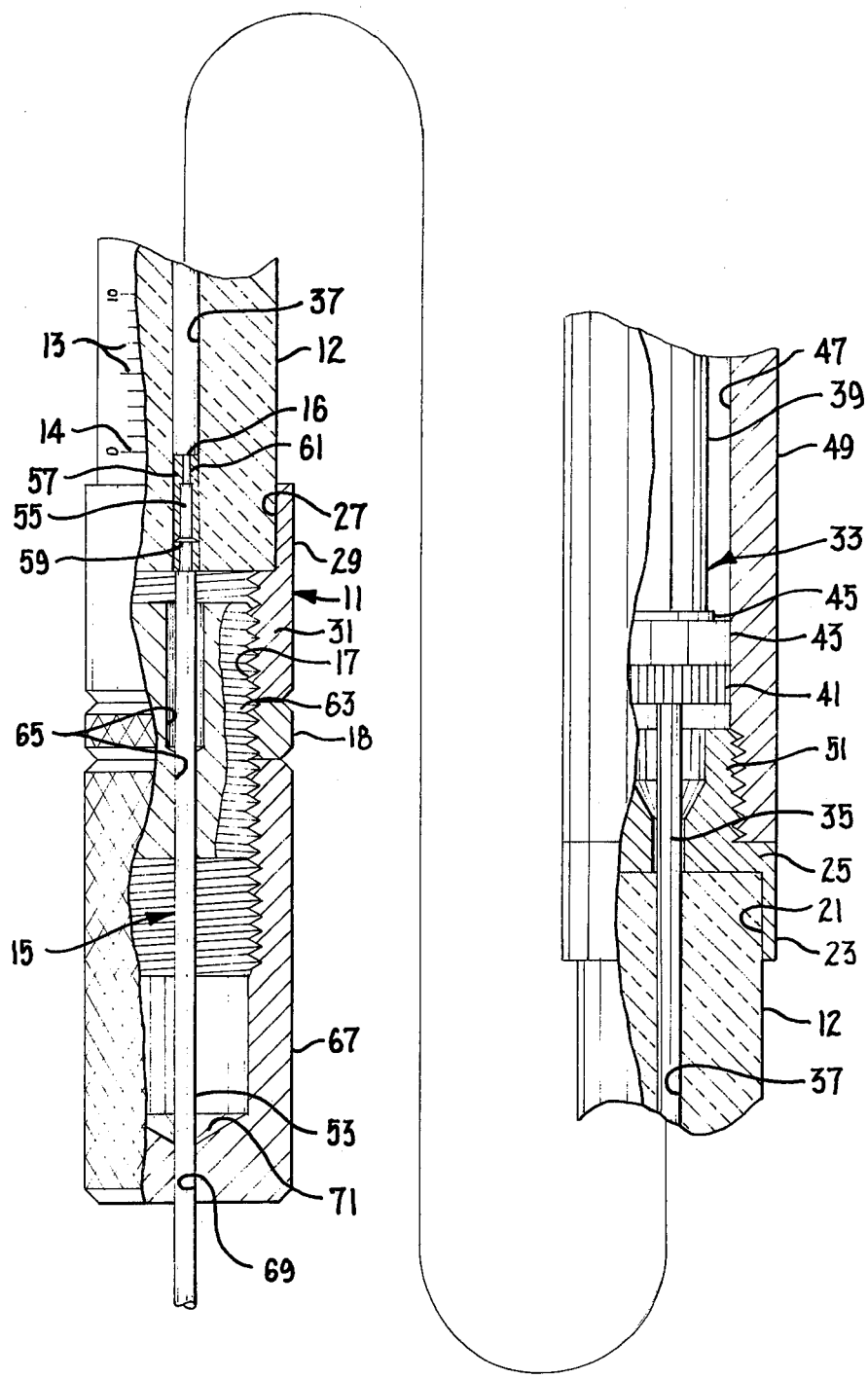

SYRINGE

This invention relates generally to syringes and, more particularly, to a syringe in which the needle assembly is readily adjustable to a zero position relative to the scale on the exterior of the glass barrel of the syrings without the necessity for utilizing special tools.

Syringes employed for various purposes often incorporate a hollow barrel with markings thereon for indicating the volume of a fluid held within the barrel. The fluid is expelled from the barrel through a hollow needle assembly by depression of a plunger and the markings on the barrel indicate precisely the amount of fluid dispensed.

Typically, the needle of the needle assembly through which the fluid is dispensed is made of sufficiently small diameter so that no liquid is normally retained within the hollow needle, or that any liquid retained therein is of negligible quantity. The needle is secured to the body of the syringe and a tip of the needle projects within the hollow barrel. For precise calibration, it is usually necessary to line up the end of the needle within the hollow body with a reference mark or zero mark. Because it is also necessary that the needle be firmly secured to the syringe body, adjustment of the needle to ensure that the end thereof is properly lined up with the reference mark may be difficult and may require special tools.

It is an object of the present invention to provide an improved syringe.

Another object of the invention is to provide an improved syringe in which the hollow needle is readily adjustable to a zero position relative to the scale on the exterior of the transparent barrel without the necessity for utilizing special tools.

A more specific object of the invention is to provide an improved syringe in which the needle assembly is adjustably secured in the body of the syringe for allowing manual adjustment of the position of the needle assembly with respect to the body for lining up one end of the needle assembly with a reference mark in the transparent hollow barrel, and to permit the needle assembly to be locked in such position.

Other objects of the invention will become apparent to those skilled in the art from the following description, taken in connection with the accompanying drawings wherein the sole FIGURE is a full section view of two axially displaced portions of a syringe constructed in accordance with the invention.

Very generally the syringe of the invention includes a hollow body 11 having a transparent hollow barrel 12 with markings 13 thereon for indicating the volume of a fluid held in the hollow body. The markings include a reference mark 14. A hollow needle assembly 15 extends into the body and has one end 16 positioned within the hollow barrel 12. Means 17 adjustably secure the needle assembly in the body and allow manual adjustment of the position of the needle assembly with respect to the body for lining up the one end 16 of the needle assembly with the reference mark 14. Means 18 provide for locking the position of the needle assembly with respect to the body.

Referring now more particularly to the drawing, two axially separated portions of a typical syringe are illustrated in section. The body 11 of the syringe includes the transparent hollow barrel 12. At each end of the barrel 12, which is cylindrical in shape, the barrel is received in a portion of the body which extends axially therefrom. Thus, at the upper end of the barrel 12, the barrel is received in a recess 21 formed by the cylindrical wall 23 of an upper body portion 25. The barrel 12 is secured in the recess 21 by any suitable means, such as a forec-fit or epoxy adhesive. Similarly, the lower end of the barrel 12 is received and secured in a recess 27 formed by the cylindrical wall 29 of a lower body portion 31.

For the purpose of expelling tje fluid contained within the hollow barrel 12, a plunger assembly 33 is employed. The plunger assembly includes a plunger rod 35 which extends within the axial central bore 37 of the barrel 12 and which is of a diameter to provide a sealed sliding fit in the bore 37. The plunger rod 35 is suitably secured to a stem 39 of the plunger assembly 33 by means of a knurled nut 41, a stop 43, and a washer 45. The stop 43 has an outer diameter conforming with the inner bore 47 of a tubular holder 49 and slides axially therein to guide the stem 39 and the plunger rod 35. Axial movement of the plunger assembly 33 with respect to the holder 49 and hence with respect to the body 11 is accomplished by a suitable manually or mechanically operated device, not shown, affixed to the end of the stem 39. The holder 49 is secured to the upper body portion 25 by threadably mating on a reduced diameter portion 51 of the upper body portion 25.

The needle assembly 15 includes a needle 53 which extends axially of the syringe. The needle 53 has a reduced diameter section 55 at one end thereof upon which is fitted a tip 57. The tip 57 is secured on the reduced diameter section 55 by an annulus 59 and includes a passage 61 communicating from the hollow interior of the needle 53 to the internal bore 37 of the barrel 12. The diameter of the passage 61 and the internal diameter of the needle 53 are such as to preclude leakage of fluid from the internal passage 37 in the barrel 12 unless sufficient pressure is produced therein by depression of the plunger assembly 33.

The needle assembly 15 includes a needle hub 63 having a central axial passage 65 of stepped diameters. The needle 53 is staked to the hub 63 in the portion of the passage 65 of lesser diameter. Threads on the external surace of the hub 63 mate with the internal threads 17 on the lower body portion 31. Rotation of the hub 63 thereby moves the needle assembly 15 axially with respect to the body 11 and therfore axially with respect to the barrel 12. This adjusts the position of the end 16 of the needle assembly 15 with respect to the barrel 12. It is thereby possible to line up the end 16 even with the zero or reference mark 14 to precisely adjust the volume of the internal bore 37 of the barrel 12 in conformity with the gradations or marks 13 on the exterior surface of the barrel.

For the purpose of locking the hub 63 and therefore the barrel assembly 15 in place after proper adjustment of the position of the end 16 with respect to the reference mark 14, the jam nut 18 is provided. The jam nut is threaded on the exterior threads of the hub 63 and may be tightened to press against the end of the lower body portion 31. This tightly secures the hub 63 with respect to the body 11, and hence secures the needle assembly 15 with resepct thereto.

Completing the assembly is a retainer nut 67 which is of generally cup-shaped configuration and contains internal threads which mate with the external threads on the hub 63. A passage 69 through the closed end 71 of the cup-shaped retainer nut 67 permits passage of the needle 53 therethrough. The retainer nut 67 may be tightened against the jam nut 18 to ensure a tight assembly and lock the jam nut in place. The external surfaces of the jam nut and the retainer nut are knurled for convenient mechanical adjustment.

The advantages of the invention are particularly related to the initial assembly of the syringe, however, it is also possible to adjust the position of the needle assembly at later times if it comes out of adjustment. In assembling the syringe of the invention, the upper and lower body portions 25 and 31, respectively, are bonded to the glass barrel 12 by suitable adhesive. The needle assembly 15 is then formed by staking and bonding the needle 53 to the hub 63 and the tip 57 is pressed onto the specially machined end 55 of the needle 53. The needle assembly 15 is then secured to the body 11 by threading the hub 63 into the lower body portion 31 until the free end 16 of the needle assembly is visually sighted to be adjacent the reference or zero mark 14 on the barrel 12. The jam nut 18 is then installed and tightened against the body and the retainer nut 67 is installed and tightened against the jam nut. This locks the hub 63 in place providing a secure assembled syringe.

It may therefore be seen that the invention provides an improved syringe which is readily manufactured and in which the hollow needle assembly is readily adjusted to a zero position relative to the scale on the exterior of the transparent barrel without the necessity of utilizing special tools.

Various modifications of the invention in addition to those shown and described herein will become apparent to those skilled in the art from the foregoing description and accompanying drawing. Such modifications are intended to fall within the scope of the appended claims.

What is claimed is:

1. A syringe comprising a syringe body including a transparent hollow barrel having markings thereon for indicating the volume of a fluid held in said hollow body, said markings including a reference mark, a hollow needle assembly extending into said body and having one end positioned in said hollow barrel, said needle assembly having threaded adjusting means adjustably securing said needle assembly in said hollow body and being rotatable therein for allowing manual adjustment of the position of said needle assembly with respect to said body for lining up said one end of said needle assembly with said reference mark, and threaded locking means on said threaded adjusting means for engaging said body and locking the position of said needle assembly with respect to said body.

2. A syringe according to claim 1 wherein said needle assembly includes a tip at said one end thereof disposed within said hollow body in a slidable sealed relationship thereto.

3. A syringe according to claim 2 wherein said tip is of generally cylindrical configuration having an internal opening therein, and wherein said needle assembly further includes a needle a portion of which is received and secured in said internal opening.

4. A syringe according to claim 1 wherein said hollow body includes an internal axial bore, wherein said needle assembly includes a tip at said one end thereof disposed within said bore in a slidable sealed relationship thereto, wherein said tip is of generally cylindrical configuration having first and second internal openings therein, and wherein said needle assembly further includes a needle a portion of which is received and secured in one of said internal openings communicating with said bore through the other of said internal openings in said tip.

5. A syringe according to claim 1 wherein said threaded adjusting means comprise an externally threaded hub within said body, and wherein said body includes a plurality of internal threads mating with said externally threaded hub.

6. A syringe according to claim 5 wherein a portion of said threaded hub extends axially externally of said body, and wherein said threaded locking means comprise a jam nut threadably secured on said hub and axially engageable with said body.

7. A syringe according to claim 1 wherein said threaded adjusting means comprise an externally threaded hub within said body, wherein said body includes a plurality of internal threads mating with said externally threaded hub, wherein a portion of said threaded hub extends axially externally of said body, wherein said threaded locking means comprise a jam nut threadably secured on said hub and axially engageable with said body, and a retainer nut threadably secured on said hub and axially engageable with said jam nut.

8. A syringe comprising, a syringe body including a transparent barrel having an axial bore therein and having markings thereon for indicating the volume of a fluid held in the hollow body, said markings including a reference mark, a hollow needle assembly including a needle, an externally threaded hub secured on said needle, and a tip secured to one end of said needle and extending into said bore, a pluraltiy of internal threads on said body mating with said externally threaded hub to allow manual adjustment of the position of said needle assembly with respect to said body for lining up said tip with said reference mark, and a jam nut threadably secured on said hub and axially engageable with said body for locking the position of said needle assembly with respect to said body.

* * * * *